(12) United States Patent
Uchida et al.

(10) Patent No.: US 8,241,684 B2
(45) Date of Patent: *Aug. 14, 2012

(54) PREVENTIVE AND/OR THERAPEUTIC AGENT FOR INFLAMMATORY BOWEL DISEASES

(75) Inventors: Masayuki Uchida, Odawara (JP); Seiko Narushima, Ichikawa (JP); Keiko Morikubo, Odawara (JP)

(73) Assignee: Meiji Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/170,771

(22) Filed: Jun. 28, 2011

(65) Prior Publication Data

US 2011/0257269 A1      Oct. 20, 2011

Related U.S. Application Data

(63) Continuation of application No. 11/578,028, filed as application No. PCT/JP2005/007183 on Apr. 13, 2005, now Pat. No. 8,025,911.

(30) Foreign Application Priority Data

Apr. 13, 2004   (JP) ................................ 2004-117755

(51) Int. Cl.
  *A01N 63/02*   (2006.01)
(52) U.S. Cl. ....... 424/780; 424/93.4; 424/115; 424/535; 435/252.1
(58) Field of Classification Search .................. None
See application file for complete search history.

(56) References Cited

U.S. PATENT DOCUMENTS

| | | |
|---|---|---|
| 6,210,719 B1 | 4/2001 | DeLang et al. |
| 6,991,820 B2 | 1/2006 | Ming et al. |
| 7,241,809 B2 | 7/2007 | Okada et al. |
| 2005/0137261 A1 | 6/2005 | Okada et al. |

FOREIGN PATENT DOCUMENTS

| | | |
|---|---|---|
| JP | 2003 504409 | 2/2003 |
| WO | 01 28547 | 4/2001 |
| WO | 03 016544 | 2/2003 |

OTHER PUBLICATIONS

Okada, Yoshikiyo et al.,"Propionic Acid Bacteria ni Yoru Nyusei Hakkobutsu Seibun DHNA no DSS Choen ni Taisuru Koensho Sayo no Kento", Digestive Organ and Immunology, vol. 40, pp. 58-60, 2003.

D'Argenio, Giuseppe et al.,"Short-Chain Fatty Acid in the Human Colon. Relation to Inflammatory Bowel Diseases and Colon Cancer", Advance in Experimental Medicine and Biology, Advance in Nutrition and Cancer 2, vol. 472, pp. 149-158, 1999.
Mortensen Brobech P. et al.,"Short-Chain Fatty Acids in the Human Colon: Relation to Gastrointestinal Health and Disease", Scandinavian Journal of Gastroenterology, vol. 31, No. 216, pp. 132-148, 1996.
Uchida et al, J Pharmacol Sci, 2005, vol. 97, pp. 285-288.
Okada et al, Gastroenterology, vol. 126, No. 4, Supp.2, 2004, p. A576, XP002534919.
Uchida et al, J. of Pharmacol. Sci., vol. 99, No. 4, 2005, pp. 329-334, XP002534920.
Sakata et al, Exp. Anim., vol. 48, No. 2, 1999, pp. 95-100.
Kibe et al, FEMS Microbiology Letters, vol. 235, 2004, pp. 139-146.
Benno et al, Microbiol. Immunol., vol. 36, No. 7, 1992, pp. 683-694.
Salzman et al, Microbiology, vol. 148, 2002, pp. 3651-3660.
Bercik et al, Gastroenerol Clin North Am, 2005, vol. 34, No. 2.
Kaneko et al, J Dairy Science, 1994, vol. 77, p. 393-404.
Hojo et al, Biosci Microflora, 2002, vol. 21, No. 2. pp. 115-120.
Gossens et al, Scand J. Gastroenterol, 2003, Supp. vol. 239, p. 15-23.
Isawa et al, Bioscience. Biotechnol. Biochem., 2002, vol. 66, No. 3, pp. 679-681.
Petschow et al, J. Clin Microbiology, 1990, vol. 28, No. 2, pp. 287-292.
Kirjavainen et al, Gut, 2002, vol. 51, pp. 51-55.
Proulx et al, Lait, 1994, vol. 74, pp. 139-152.
Merck Manual of Diagnosis and Therapy, Japanese version, 17th Edition, 1999, pp. 305 and 309, (with English translation).
Merck Manual of Diagnosis and Therapy, 17th Edition, 1999, Section 3, Gastrointestinal Disorders, pp. 302-312, published by Merck Research Laboratories, Whitehouse Station, NJ.
Sulpiride Tablets 200mg, 400mg http://www.medicines.org.uk/EMC/medicine/18769/PIL/Sulpiride+Tablets+200mg%2c+400mg+(Wockhardt+UK+Ltd)/ Jan. 2008 (2 pages).
Sulpiride Tablets 50 mg http://www.tanabe.co.jp/product/di/productdetail.php?id=109.
Patient Information Leaflet (PIL) of Boots Aspirin Caplets 300mg http://www.medicines.org.uk/EMC/medicine/21620/XPIL/Aspirin+Caplets+300mg+(Boots+Company+plc)/ Dec. 2009 (3 pages).
Aspirin "Bayer" http://www.bayer-hv.jp/hv/products.
Patient Information Leaflet (PIL) of Boots Aspirin 75 mg Enteric Coated Tablet http://www.medicines.org.uk/EMC/medicine/22824/XPIL/Boots+Aspirin+75mg+Enteric+Coated+Tablets+(28s)/ May 2009 (3 pages).
Bayaspirin 100mg http://www.bayer-hv.jp/hv/products.

*Primary Examiner* — Kade Ariani
(74) *Attorney, Agent, or Firm* — Oblon, Spivak, McClelland, Maier & Neustadt, L.L.P.

(57) ABSTRACT

The present invention relates to a preventive and/or a therapeutic agent for inflammatory bowel diseases containing a fermentation product of a propionic acid bacterium as an active ingredient.

13 Claims, 2 Drawing Sheets

\* : It is found significant versus group given non-fermented product (p < 0.05: Dunnet's multiple comparison test)
\*\* : It is found significant versus control group (p < 0.01: Dunnet's multiple comparison test)

\*、\*\* : It is found significant versus control group (p < 0.05, 0.01: Dunnet's multiple comparison test)

*: It is found significant versus control group ($p < 0.05$: Student's t-test)

PREVENTIVE AND/OR THERAPEUTIC AGENT FOR INFLAMMATORY BOWEL DISEASES

This application is a continuation application of U.S. patent application Ser. No. 11/578,028, filed Oct. 12, 2006, now U.S. Pat. No. 8,025,911, issued Sep. 27, 2011, which is a national stage application of PCT/JP2005/007183, filed Apr. 13, 2005.

TECHNICAL FIELD

The present invention relates to a preventive and/or a therapeutic agent for inflammatory bowel diseases such as ulcerative colitis and Crohn's disease.

BACKGROUND ART

Inflammatory bowel disease (IBD) is a general name for diseases of unknown causes that are represented by ulcerative colitis and Crohn's disease which cause chronic inflammation and/or ulceration of the mucosa of the large and small intestines. The majority of the patients are affected at relatively young ages, i.e., in their teens or twenties, and they develop clinical symptoms such as diarrhea, fever, and abdominal pain and systemic inflammatory symptoms. There have been problems that the patients become unable to efficiently absorb nutrients of foods and drinks taken orally, and their social life is seriously affected by food restriction and increased stool frequency. As to the possible causes of IBDs, theories that have been reported include autoimmune abnormality and enterobacteria, which still remain unclear, no treatment method leading to complete cure has been found up until today (Non-patent Document 1).

As a therapeutic agent for IBDs such as ulcerative colitis, salazosulfapyridine, 5-aminosalicylic acid, steroids, immunosuppressive agents, and the like are commonly used. However, sufficient treatment effect cannot be obtained by these therapeutic agents, and side effects caused by long term administration of steroids and immunosuppressive agents become a serious problem (Non-patent Document 1).

Recently, it has been shown that *Propionibacterium freudenreichii*, one of propionic acid bacteria, produces bifidogenic growth stimulators (BGSs) and that the active component thereof is 1,4-dihydroxy-2-naphthoic acid (DHNA). DHNA is known to have effects of promoting the growth of bifidobacteria and improving inflammatory conditions of the mucosa in IBDs as well as suppressing infiltration of activated immune cells (for example, refer to Patent Document 1). Further, DHNA has been reported to alleviate abdominal discomfort associated with milk intake in milk intolerance and to be useful for prevention and/or therapy of metabolic bone diseases (refer to the same reference). Since this DHNA is produced by propionic acid bacteria in large amounts both intracellularly and extracellularly, a fermentation method using a propionic acid bacterium is attracting attention as a highly safe production method of DHNA. A fermentation product of a propionic acid bacterium obtained by a fermentation technique contains DHNA at a high concentration and is approved as a food for specified health use that regulates the functions of the intestines.

[Patent Document 1] WO publication 03/016544 pamphlet
[Non-patent Document 1] Shoukakibyou seminar 77 Enshousei Chousikkan-Atarashii Shiten (in Japanese) (Seminar on Gastrointestinal Diseases 77 Inflammatory Bowel Disease-A New View) Tadao Baba, Ed., Herusu Shuppan, Co., Inc. 1999

DISCLOSURE OF THE INVENTION

Accordingly, the object of the present invention is to provide a highly safe preventive and/or a highly safe therapeutic agent for inflammatory bowel diseases (IBDs).

As a result of assiduous research, the present inventors perfected the present invention by discovering that a fermentation product of a propionic acid bacterium is effective for prevention and/or therapy of IBDs.

That is, the present invention provides a preventive and/or a therapeutic agent for IBDs containing a fermentation product of a propionic acid bacterium as an active ingredient as well as a food for prevention and/or therapy of IBDs.

Further, the present invention provides use of a fermentation product of a propionic acid bacterium for production of a preventive and/or a therapeutic agent for IBDs as well as a food for prevention and/or therapy of IBDs.

Still further, the present invention provides a method for prevention and therapy of IBDs characterized in that an effective amount of a fermentation product of a propionic acid bacterium is administered.

The preventive and/or the therapeutic agent for IBDs of the present invention can safely prevent and/or treat IBDs such as ulcerative colitis.

BEST MODE FOR CARRYING OUT THE INVENTION

Figure 1:
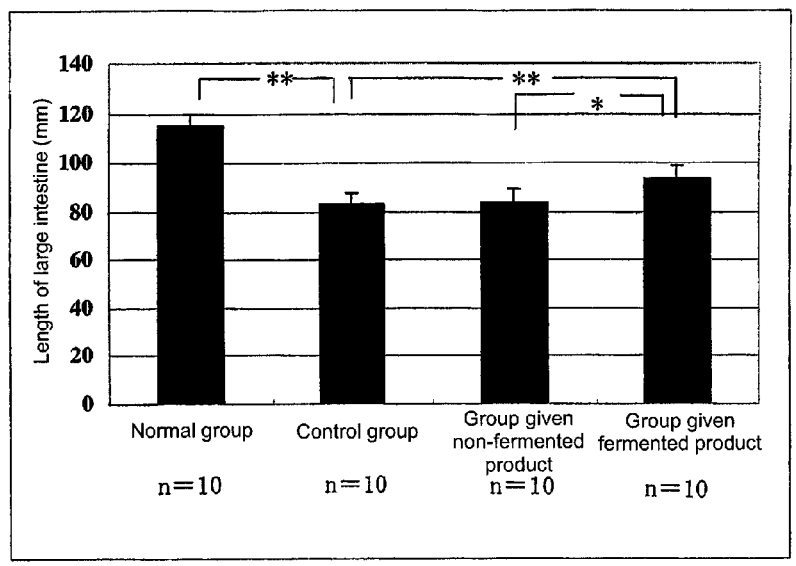
FIG. 1 is a diagram showing changes in the length of the large intestine caused by administration of a whey fermentation product of a propionic acid bacterium in DSS colitis mice where an average±standard error of the length of the large intestine (mm) of each group is shown.

A fermentation product of a propionic acid bacterium that is an active ingredient of the present invention can be produced according to the known production method disclosed in WO publication 03/016544 pamphlet or the like. In the present specification, "a fermentation product of a propionic acid bacterium" includes culture itself obtained by fermentation of the propionic acid bacterium, processed matter thereof, for example, filtrate, supernatant, or precipitates of the culture as it is or the culture obtained after removal of bacteria or sterilization, or concentrates thereof after concentration with an evaporator and the like, pastes, diluted matter or dried matter (by vacuum drying, spray drying, freeze-drying, etc.), and the like.

The propionic acid bacterium used in the production of the fermentation product of a propionic acid bacterium is not particularly limited as long as it produces DHNA, but is preferably a bacterium belonging to the genus *Propionibacterium*. Examples of the bacterium belonging to the genus *Propionibacterium* include bacteria for producing cheese such as *Propionibacterium freudenreichii*(*P. freudenreichii*), *P. thoenii*, *P. acidipropionici*, and *P. jensenii*, or *P. avidum*, *P.*

*acnes, P. lymphophilum, P. granulosam*, and the like. Among these, *P. freudenreichii* is preferred, *P. freudenreichii* IFO 12424 or *P. freudenreichii* ATCC 6207 is more preferred, and *P. freudenreichii* ET-3 (FERM BP-8115) is particularly preferred.

The present inventors deposited *P. freudenreichii* ET-3 strain at the International Patent Organism Depositary, National Institute of Advanced Industrial Science and Technology, an Independent Administrative Institution. The contents specifying the deposit are described below.

(1) Name of Depositary Institution: International Patent Organism Depositary, National Institute of Advanced Industrial Science and Technology, an Independent Administrative Institution (2) Address of Depositary Institution: Postal code 305-8566, Tsukuba Central 6, 1-1-1 Higashi, Tsukuba, Ibaraki, Japan (3) Accession Number: FERM BP-8115
(4) Identification Reference: ET-3
(5) Date of Deposit: Aug. 9, 2001

Among other strains, the strain of a name with the suffix ATCC is a standard strain obtained from the American Type Culture Collection, and the strain of a name with the suffix IFO is a standard strain obtained from the Institute for Fermentation, Osaka.

Next, a propionic acid bacterium is cultured aerobically or anaerobically in a culture medium containing nutrients that can support the growth of common microorganisms. As the nutrients, known nutrients that are conventionally used for culturing microorganisms can be used. As the culture medium used for fermentation of the propionic acid bacterium, a culture medium or the like in which whey powder, casein, skim milk powder, whey protein concentrates, whey protein isolates, and the like, and additionally, yeast extract, peptone such as Trypticase, appropriate amounts of sugars and minerals including glucose, lactose, lactase-treated lactose, whey minerals, and the like can be used. Particularly, a fermentation product of the propionic acid bacterium in a medium supplemented with whey powder is hereinafter also referred to as whey fermentation product of the propionic acid bacterium.

For the culture method, although a variety of known aerobic or anaerobic culture methods can be used, an aerobic or anaerobic culture method using a liquid culture medium is preferred in view of large scale production. The culture temperature is preferably from ca. 20 to 40 degrees C., and the pH of the culture medium is preferably from neutral to weakly acidic (preferably from pH 5.5 to 7.5). Although the culture solution may be used immediately after stopping the culture, it is preferred to use the culture solution after cooling (3 to 20 degrees C., preferably ca. 10 degrees C.) and storing for approximately 2 to 4 weeks.

The fermentation product of the propionic acid bacterium obtained by the above method preferably contains DHNA at 0.001 to 50 w/w % in its solid content, and particularly preferably contains DHNA at 0.008 to 10 w/w %.

The fermentation product of the propionic acid bacterium was found to have an excellent preventive and/or therapeutic effect on a dextran sulfate sodium (DSS) enteritis or 2,4,6-trinitrobenzenesulfonate (TNBS) enteritis that is widely known as a model of IBDs as shown in examples described later. Specifically, the fermentation product of the propionic acid bacterium suppressed the shortening of the length of the large intestine that is a typical symptom of the DSS enteritis and significantly reduced the size of ulcer that is a typical symptom of the TNBS enteritis. Further, the fermentation product of the propionic acid bacterium showed a therapeutic effect on the DSS enteritis approximately equal to that with 20 times higher dosage of DHNA compared with DHNA contained in the fermentation product of the propionic acid bacterium.

Examples of IBDs that become treatment targets of the present invention include ulcerative colitis, Crohn's disease, and the like. Further, intestinal diseases due to pathogenic microorganisms, drugs, blood circulation disorder, radiation, and chemical and physical factors, which are understood as IBDs in a broad sense, may also be included.

The fermentation product of the propionic acid bacterium can be utilized in either form of pharmaceutical drug or food and drink. For example, various IBDs can be remedied by directly taking the fermentation product of the propionic acid bacterium as a pharmaceutical drug or by directly taking food for special dietary uses such as food for specified health uses and food with nutrient function claims. Further, the fermentation product of the propionic acid bacterium may be added to various foods (milk, soft drink, fermented milk, yogurt, cheese, bread, biscuit, cracker, pizza crust, etc.), and these may be taken as well.

For foods containing the fermentation product of the propionic acid bacterium, water, proteins, sugars, lipids, vitamins, minerals, organic acids, organic bases, fruit juices, flavors, and the like can be used. The proteins include, for example, animal and plant proteins such as whole milk powder, skim milk powder, partially skimmed milk powder, casein, whey powder, whey protein, whey protein concentrates, whey protein isolates, α-casein, β-casein, κ-casein, β-lactoglobulin, α-lactoalbumin, lactoferrin, soy bean protein, chicken egg protein, and meat protein, and hydrolysates thereof; and various components derived from milk such as butter, whey minerals, cream, whey, non-protein nitrogens, sialic acids, phospholipids, and lactose are included. The sugars include, for example, sucrose, glucose, fructose, sugar alcohols, maltose, oligosaccharides, modified starch (in addition to dextrin, soluble starch, British starch, oxidized starch, starch ester, starch ether, etc), and dietary fiber. The lipids include, for example, animal oil and fat such as lard and fish oil, and plant oil and fat such as palm oil, safflower oil, corn oil, rapeseed oil, coconut oil, and fractionated oils, hydrogenated oils and transesterified oils thereof. The vitamins include, for example, vitamin A, vitamin B group, vitamin C, erythorbic acid, vitamin D group, vitamin E, vitamin K group, vitamin P, vitamin Q, niacin, nicotinic acid, pantothenic acid, biotin, inosite, choline, and folic acid, and the minerals include, for example, calcium, potassium, magnesium, sodium, chlorine, copper, iron, manganese, zinc, selenium, fluorine, silicon, and iodine. The organic acids include, for example, malic acid, citric acid, lactic acid, and tartaric acid. These components may be used as a single selected component or in combination of two or more selected components. For these components, synthetic products or, as needed, foods containing these in a large amount may be used.

When the fermentation product of the propionic acid bacterium is used as a pharmaceutical drug, various administration forms are available. The forms can include, for example, oral administration in tablets, capsules, granules, powder, and syrup. These various preparations can be formulated, in addition to the main ingredient, using conventionally known pharmaceutical adjuvants that can be commonly used in the field of pharmaceutical formulation technology such as excipient, binder, disintegrating agent, lubricant, taste-modifying agent, odor-modifying agent, solubilizing agent, suspending agent, and coating agent.

When the preparation of the fermentation product of the propionic acid bacterium is applied to human, an effective preventive and/or therapeutic dose of the fermentation product of the propionic acid bacterium is generally 10 to 5000 mg per adult per day as the solid content, preferably 100 to 1000 mg, more preferably 200 to 800 mg, though it varies depending on the age and condition of patients who undergo prevention and/or therapy.

EXAMPLES

Hereinafter, the present invention is explained in detail by way of examples, but the present invention is not limited to these.

Example 1

(1) Materials and Methods (Production of Whey Fermentation Product of the Propionic Acid Bacterium)

An aqueous solution containing whey powder (10 w/w %) and Protease Amano A (product of Amano Enzyme Inc.) was subjected to enzymatic hydrolysis for 2 hours at 47 degrees C. (pH 6.6). Then, the enzyme was inactivated by heating for 10 min at 85 degrees C. Subsequently, brewers yeast extract (final concentration 0.10 w/w %, product of Asahi Breweries, Ltd.) and ammonium sulfate (final concentration 0.27 w/w %) were added and sterilized for 7 min at 121 degrees C. after adjusting its pH to 6.7. To this culture medium, an activated culture fluid of $P.\ freudenreichii$ ET-3 (FERM BP-8115) (bacterial concentration: $2–5\times10^9$ cfu/mL) was inoculated at 2 v/w % and cultured anaerobically for 72 hours at 37 degrees C. under nitrogen atmosphere. This culture fluid was obtained as a whey fermentation product of the propionic acid bacterium (content of solid matter: 10 w/v %, DHNA content in solid matter: 0.01 w/w %). Note that for the activated culture fluid of $P.\ freudenreichii$ ET-3, the same culture medium as above was used.

For a non-fermented product, the culture fluid that had been incubated without inoculating the propionic acid bacterium was used.

(Test Animal)

Seven-week-old female BALB/c strain mice were subjected to experiments.

(Preparation of Mouse Colitis Model and Administration of Whey Fermentation Product of the Propionic Acid Bacterium)

An aqueous solution of 3% dextran sulfate sodium (DSS, MW 40,000) was prepared, and the mice were allowed to take the solution as drinking water ad libitum for 8 days to prepare a mouse colitis model (hereinafter, also referred to as colitis mouse). Among the colitis mice, a group given the whey fermentation product of the propionic acid bacterium (the group given fermented product in FIG. 1) received the whey fermentation product of the propionic acid bacterium orally at 0.3 mL/body (3 μg/body on DHNA basis) twice a day for 8 days from the initial day of DSS administration. Among the colitis mice, a group given the non-fermented product received the non-fermented product orally at 0.3 mL/body twice a day for 8 days from the initial day of DSS administration. Among the colitis mice, a control group received distilled water orally at 0.3 mL/body twice a day for 8 days from the initial day of DSS administration. In addition, mice that were allowed to take distilled water in place of DSS ad libitum and received orally the same volume of distilled water in place of the whey fermentation product of the propionic acid bacterium or the non-fermented product according to the same administration schedule as described above served as a normal group.

(2) Evaluation (Length of Large Intestine)

After completion of the administration, the large intestine was taken out, and the length (mm) from the cecum to the anus was measured. The results are shown in FIG. 1.

(3) Results and Discussion

As is evident from FIG. 1, the length of the large intestine was significantly shortened in the control group compared with the normal group. On the other hand, shortening of the length of the large intestine in the group given the whey fermentation product of the propionic acid bacterium was significantly suppressed compared with the control group and the group given the non-fermented product. Therefore, the whey fermentation product of the propionic acid bacterium was found to have a therapeutic effect on the DSS enteritis model.

Example 2

(1) Materials and Methods (Test Animal)

Seven-week-old male SD strain rats were subjected to experiments.

(Preparation of Rat Colitis Model and Administration of Whey Fermentation Product of the Propionic Acid Bacterium)

An aqueous solution of 3% dextran sulfate sodium (DSS, MW 5,000) was prepared, and the rats were allowed to take the solution as drinking water ad libitum for 10 days to prepare a rat colitis model (hereinafter, also referred as colitis rat). Subsequently, the drinking water was replaced with an aqueous solution of 1% dextran sulfate sodium (DSS, MW 5,000), and the rats were allowed to take the solution ad libitum for further 3 days. Among the colitis rats, a group given the whey fermentation product of the propionic acid bacterium (the group given fermented product in FIG. 2) received the whey fermentation product of the propionic acid bacterium described in Example 1 orally at 3 mL/body (30 μg/body on DHNA basis) twice a day for 3 days from the initial day of 1% DSS administration. Among the colitis rats, a group given DHNA received DHNA (product of Wako Pure Chemical Industries, Ltd.) orally at 600 μg/body twice a day for 3 days from the initial day of 1% DSS administration. DHNA was dissolved in an aqueous solution of 0.25% ascorbic acid for stabilization and used after preparing the solution so that the dosage volume became 3 mL/body. Among the colitis rats, a control group received the aqueous solution of 0.25% ascorbic acid orally at 3 mL/body twice a day for 3 days from the initial day of 1% DSS administration. In addition, rats that were allowed to take distilled water in place of DSS ad libitum and received the same volume of distilled water orally in place of the whey fermentation product of the propionic acid bacterium or DHNA according to the same administration schedule as described above served as a normal group.

(2) Evaluation (Length of Large Intestine)

After completion of the administration, the large intestine was taken out, and the length (mm) of from the cecum to the anus was measured. The results are shown in FIG. 2.

(3) Results and Discussion

Figure 2:
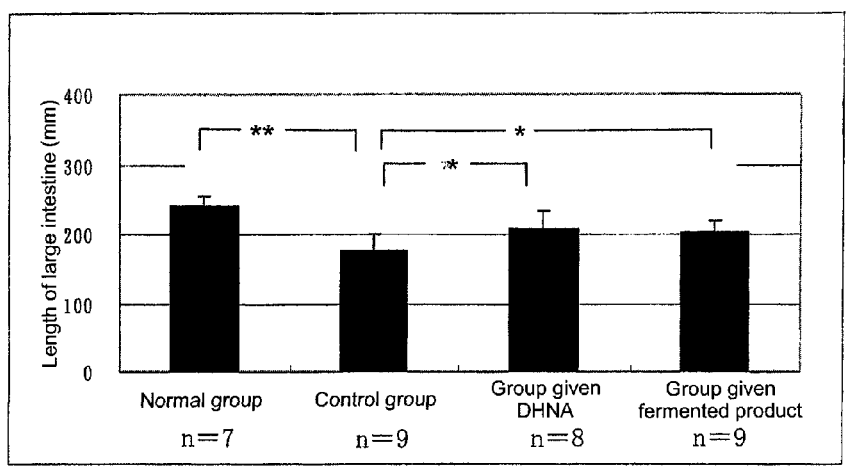
FIG. 2 is a diagram showing changes in the length of the large intestine caused by administration of the whey fermentation product of the propionic acid bacterium in DSS colitis rats where an average±standard error of the length of the large intestine (mm) of each group is shown.

As is evident from FIG. 2, the length of the large intestine was significantly shortened in the control group compared with the normal group. On the other hand, shortening of the length of the large intestine in the group given the whey fermentation product of the propionic acid bacterium was significantly suppressed compared with the group given DHNA despite the fact that an amount of only about ½₀ on DHNA basis was administered. Accordingly, it was suggested that the ingredients other than DHNA in the whey fermentation product of the propionic acid bacterium exerted an additional effect on the therapy of DSS enteritis.

Example 3

(1) Materials and Methods (Test Animal)

Six-week-old male SD strain rats were subjected to experiments.

(Preparation of Rat Colitis Model and Administration of Whey Fermentation Product of the Propionic Acid Bacterium)

The method of preparation of a rat colitis model was based on the method of Uchida et al. (Masayuki Uchida, Orie Mogami, J. Pharmacol Sci, 97, pp 285-288 (2005)).

A solution of 0.1 M 2,4,6-trinitrobenzenesulfonic acid (TNBS) (dissolved in 35% ethanol) was prepared, and this was administered intraintestinally to the large intestine of the rats at 0.2 mL/body to prepare the rat colitis model (hereinafter, also referred as colitis rat). Among the colitis rats, a group given the whey fermentation product of the propionic acid bacterium (the group given fermented product in FIG. 3) received the suspension of the whey fermentation product of the propionic acid bacterium, which had once been lyophilized and suspended in an aqueous solution of 1 w/w % gum arabic to a volume equal to the original whey fermentation product of the propionic acid bacterium described in Example 1, orally at 3 mL/body (30 μg/body on DHNA basis) twice a day for 9 days from the next day of the colitis preparation. Among the colitis rats, a control group received the aqueous solution of 1 w/w % gum Arabic orally at 3 mL/body twice a day for 9 days from the next day of the colitis preparation.

(2) Evaluation (Size of Ulcer)

After completion of the administration, the large intestine was taken out, the size (mm) of ulcer developed at an inflammatory site was measured, and the product of the length multiplied by the width was taken as an ulcer index (mm²). The results are shown in FIG. 3.

(3) Results and Discussion

Figure 3:
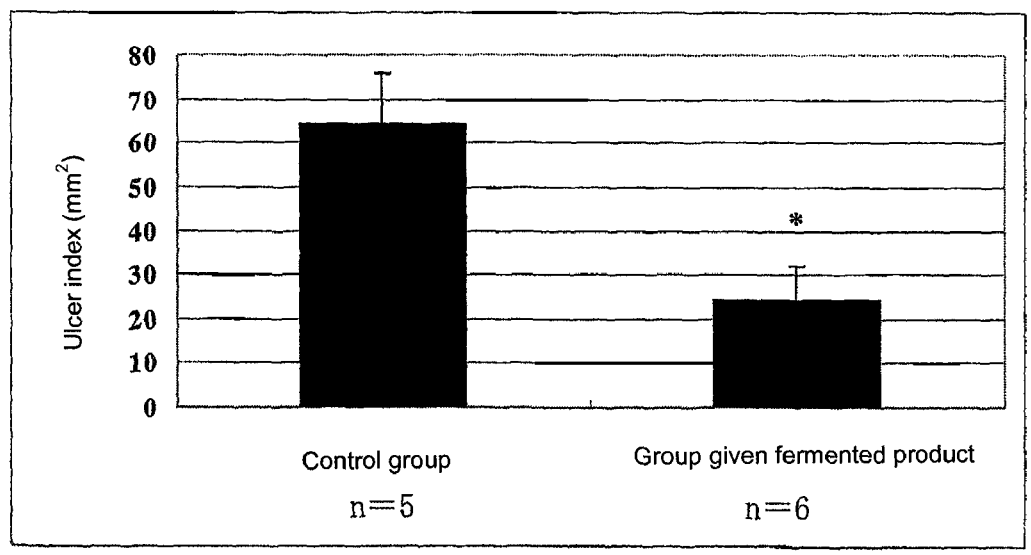
FIG. 3 is a diagram showing changes in the ulcer of the large intestine caused by administration of the whey fermentation product of the propionic acid bacterium in TNBS colitis rats where an average±standard error of the ulcer index ($mm^2$) of each group is shown.

As is evident from FIG. 3, the ulcer index was significantly reduced in the group given the whey fermentation product of the propionic acid bacterium compared with the control group.

The invention claimed is:

1. A method for treating an inflammatory bowel disease (IBD) comprising administering an effective amount of a fermentation product of a propionic acid bacterium to a subject in need thereof, wherein the fermentation product is a fermented milk whey which comprises 1,4-dihydroxy-2-naphthoic acid (DHNA) and the DHNA content in said fermentation product is equal or less than 0.01 w/w % of the solid content of the fermentation product, and wherein the propionic acid bacterium may be optionally removed after fermentation.

2. The method according to claim 1, wherein the propionic acid bacterium is a bacterium belonging to the genus *Propionibacterium*.

3. The method according to claim 1, wherein the bacterium belonging to the genus *Propionibacterium* is *Propionibacterium freudenreichii*.

4. The method according to claim 1, wherein the bacterium is *Propionibacterium freudenreichii* ET-3.

5. The method according to claim 1, wherein the fermentation product is administered in form of a pharmaceutical composition, said composition further comprises an acceptable pharmaceutical carrier.

6. The method according to claim 1, wherein the fermentation product is administered as a food or a drink additive.

7. The method according to claim 1, wherein the propionic acid bacterium is cultured aerobically or anaerobically in a culture medium supplemented with milk whey.

8. The method according to claim 1, wherein the propionic acid bacterium is cultured at a temperature of 20 to 40° C.

9. The method according to claim 7, wherein the pH of the culture medium in from 5.5 to 7.5.

10. The method according to claim 7, wherein the culture medium comprising the fermentation product is cooled to a temperature of 3 to 20° C.

11. The method according to claim 7, wherein the culture medium comprising the fermentation product is cooled to a temperature of 3 to 10° C.

12. The method according to claim 7, wherein the culture medium comprising the fermentation product is cooled to a temperature of 3 to 20° C. and stored for 2 to 4 weeks.

13. The method according to claim 1, wherein the said subject is a human, and said effective amount is 10 to 5000 mg per subject per day as solid content.

* * * * *